US011311398B2

(12) United States Patent
Sokel et al.

(10) Patent No.: US 11,311,398 B2
(45) Date of Patent: *Apr. 26, 2022

(54) HANDLE FOR MEDICAL DEVICE DEPLOYMENT

(71) Applicant: W. L. Gore & Associates, Inc., Newark, DE (US)

(72) Inventors: Justin W. Sokel, Flagstaff, AZ (US); Adam T. Storey, Seattle, WA (US); Jared L. Van Cleave, Kirkland, WA (US)

(73) Assignee: W. L. Gore & Associates, Inc., Newark, DE (US)

( * ) Notice: Subject to any disclaimer, the term of this patent is extended or adjusted under 35 U.S.C. 154(b) by 168 days.

This patent is subject to a terminal disclaimer.

(21) Appl. No.: 16/686,701

(22) Filed: Nov. 18, 2019

(65) Prior Publication Data

US 2020/0078198 A1 Mar. 12, 2020

Related U.S. Application Data

(63) Continuation of application No. 14/822,870, filed on Aug. 10, 2015, now Pat. No. 10,478,324.

(Continued)

(51) Int. Cl.
*A61F 2/966* (2013.01)
*A61F 2/95* (2013.01)

(52) U.S. Cl.
CPC ............ *A61F 2/966* (2013.01); *A61F 2/9517* (2020.05); *A61F 2002/9665* (2013.01)

(58) Field of Classification Search
CPC ..... A61F 2002/9517; A61F 2002/9505; A61B 17/2841; A61B 17/2909
See application file for complete search history.

(56) References Cited

U.S. PATENT DOCUMENTS 5,620,458 A 4/1997 Green et al.
6,203,550 B1 3/2001 Olson
(Continued)

FOREIGN PATENT DOCUMENTS

EP 1441668 B1 1/2008
EP 1915113 B1 3/2010
(Continued)

OTHER PUBLICATIONS

International Preliminary Report on Patentability received for PCT Patent Application No. PCT/US2015/044584, dated Feb. 23, 2017, 9 pages.

(Continued)

*Primary Examiner* — Majid Jamialahmadi

(57) ABSTRACT

A delivery system for endoluminal delivery of an expandable device comprising a catheter having a proximal end and an opposite distal end configured to support an expandable device, a primary sheath having a delivery position in which the primary sheath constrains the expandable device toward a collapsed configuration suitable for endoluminal delivery, and a handle including a first actuator that is actuatable to cause the expandable device to expand from the collapsed configuration, the handle further including a second actuator for operating one or more functions of the handle, wherein the second actuator is initially hidden to prevent actuation of the second actuator prior to the expandable device expanding and is configured to be revealed when the expandable device is expanded, the second actuator being actuatable once revealed.

17 Claims, 7 Drawing Sheets

Related U.S. Application Data

(60) Provisional application No. 62/036,513, filed on Aug. 12, 2014.

(56) References Cited

U.S. PATENT DOCUMENTS

| | | | |
|---|---|---|---|
| 6,352,561 B1 | 3/2002 | Leopold et al. |
| 6,551,330 B1 | 4/2003 | Bain et al. |
| 6,733,521 B2 | 5/2004 | Chobotov et al. |
| 6,911,039 B2 | 6/2005 | Shiu et al. |
| 6,974,471 B2 | 12/2005 | Van et al. |
| 7,029,488 B2 | 4/2006 | Schoenholz et al. |
| 7,081,132 B2 | 7/2006 | Cook et al. |
| 7,147,661 B2 | 12/2006 | Chobotov et al. |
| 7,655,034 B2 | 2/2010 | Mitchell et al. |
| 7,789,860 B2 | 9/2010 | Brady et al. |
| 7,837,724 B2 | 11/2010 | Keeble et al. |
| 7,938,851 B2 | 5/2011 | Olson et al. |
| 7,967,829 B2 | 6/2011 | Gunderson et al. |
| 7,976,575 B2 | 7/2011 | Hartley |
| 8,167,927 B2 | 5/2012 | Chobotov |
| 8,241,346 B2 | 8/2012 | Chobotov |
| 8,257,431 B2 | 9/2012 | Henderson et al. |
| 8,262,671 B2 | 9/2012 | Osypka |
| 8,328,861 B2 | 12/2012 | Martin et al. |
| 8,361,135 B2 | 1/2013 | Dittman |
| 8,480,725 B2 | 7/2013 | Rasmussen et al. |
| 8,968,384 B2 | 3/2015 | Pearson et al. |
| 9,060,895 B2 | 6/2015 | Hartley et al. |
| 9,132,025 B2 | 9/2015 | Aristizabal et al. |
| 9,254,204 B2 | 2/2016 | Roeder et al. |
| 9,308,349 B2 | 4/2016 | Rezac et al. |
| 9,498,361 B2 | 11/2016 | Roeder et al. |
| 9,585,743 B2 | 3/2017 | Cartledge et al. |
| 9,585,774 B2 | 3/2017 | Aristizabal et al. |
| 9,675,485 B2 | 6/2017 | Essinger et al. |
| 9,681,968 B2 | 6/2017 | Goetz et al. |
| 9,700,701 B2 | 7/2017 | Benjamin et al. |
| 9,782,284 B2 | 10/2017 | Hartley et al. |
| 9,937,070 B2 | 4/2018 | Skelton et al. |
| 10,478,324 B2 * | 11/2019 | Sokel ............... A61F 2/966 |
| 2004/0138734 A1 | 7/2004 | Chobotov et al. |
| 2005/0080476 A1 | 4/2005 | Gunderson et al. |
| 2005/0283223 A1 | 12/2005 | Greenan |
| 2006/0173524 A1 | 8/2006 | Salahieh et al. |
| 2013/0261726 A1 * | 10/2013 | Alger ............... A61F 2/958 |
| | | | 623/1.11 |
| 2013/0267995 A1 | 10/2013 | Voss et al. |
| 2014/0128844 A1 | 5/2014 | Kornowski et al. |
| 2017/0172724 A1 | 6/2017 | Cartledge et al. |
| 2017/0281382 A1 | 10/2017 | Lostetter et al. |

FOREIGN PATENT DOCUMENTS

| | | |
|---|---|---|
| EP | 1358903 B1 | 11/2011 |
| EP | 2421481 A1 | 2/2012 |
| EP | 1474074 B1 | 4/2014 |
| EP | 2749251 B1 | 7/2016 |
| EP | 2956198 B1 | 11/2017 |
| WO | 2010/123664 A1 | 10/2010 |
| WO | 2014/055765 A1 | 4/2014 |
| WO | 2015/153375 A1 | 10/2015 |

OTHER PUBLICATIONS

International Search Report and Written Opinion for PCT/US2015/044584 dated Nov. 17, 2015, corresponding to U.S. Appl. No. 14/822,870, 5 pages.

* cited by examiner

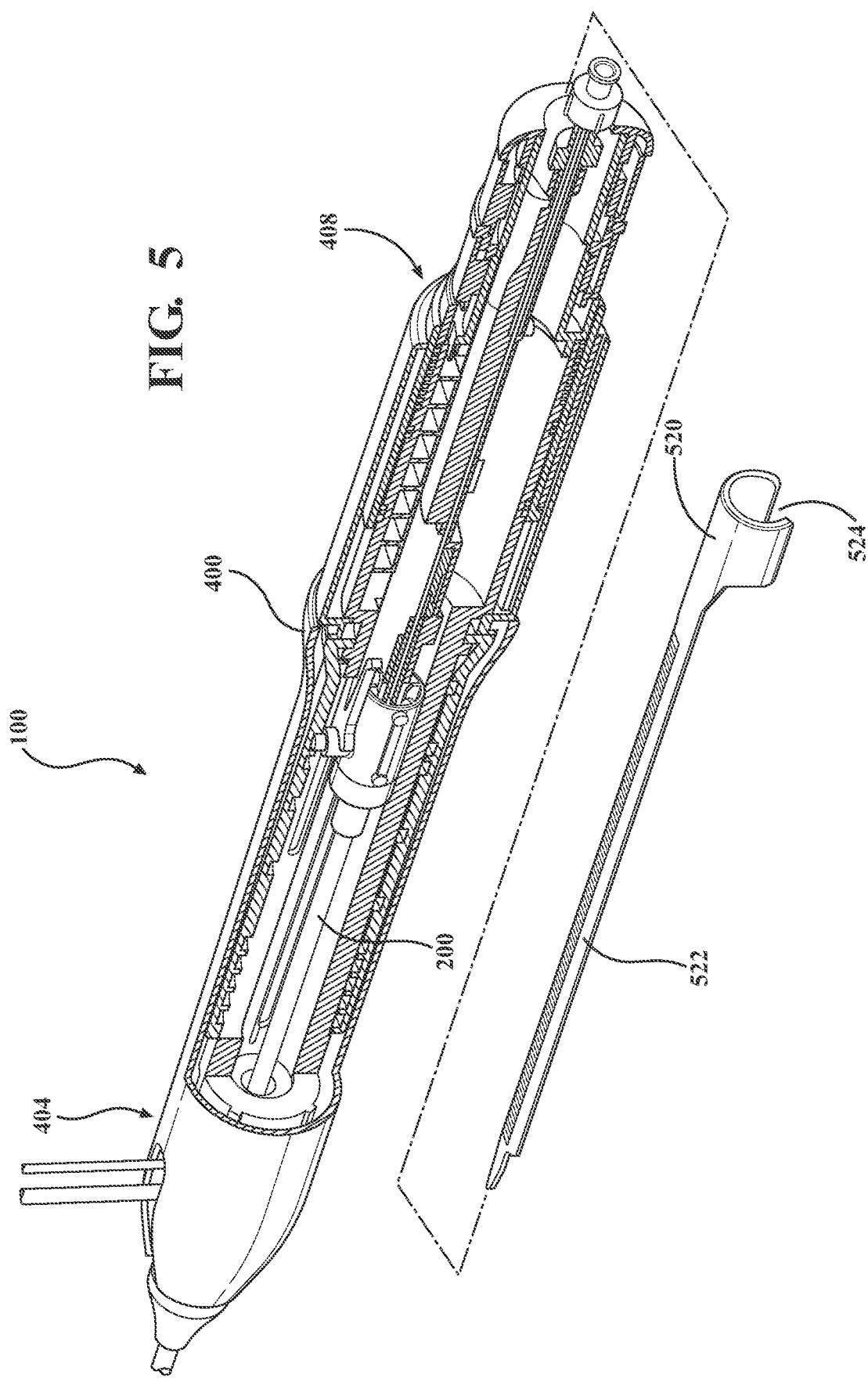

HANDLE FOR MEDICAL DEVICE DEPLOYMENT

CROSS-REFERENCE TO RELATED APPLICATION

This application is a continuation of U.S. patent application Ser. No. 14/822,870, filed Aug. 10, 2015, which claims the benefit of U.S. Provisional Application 62/036,513, filed Aug. 12, 2014, both of which are incorporated herein by reference in their entireties for all purposes.

BACKGROUND

Field

The present disclosure relates to handles for medical device deployment systems and, more particularly, to handles configured for use in multi-stage deployment systems for expandable medical devices.

Discussion

Handles for catheter-based deployment systems for endoluminal delivery of expandable devices are well-known in the art. It remains desirable to provide improved handles that can accommodate multi-stage endoluminal delivery and deployment of expandable medical devices, while improving or at least maintaining ease of operation to the clinician.

BRIEF DESCRIPTION OF THE DRAWINGS

The accompanying drawings are included to provide a further understanding of the present disclosure and are incorporated in and constitute a part of this specification, illustrate embodiments of the present disclosure and together with the description serve to explain the principles of the present disclosure.

FIGS. 1-5 are cutaway perspective views of a deployment handle for a medical device delivery system, shown in successive stages of use.

DETAILED DESCRIPTION

A handle mechanism is disclosed herein for use in connection with delivery systems for endoluminal delivery and deployment of medical devices, such as vascular endoprosthetic implants. A delivery system in accordance with the present disclosure can include a first actuator for selectively actuating a first tubular member and a second actuator for selectively actuating a second tubular member, wherein the second actuator is initially hidden and subsequently presented for use in response to operation of the first actuator.

Referring to FIGS. 1-5, for example, a medical device delivery system is generally indicated at 100. The delivery system 100 includes a catheter (not shown) having a proximal end and an opposite distal end. The distal end of the catheter is configured for supporting at least one expandable, endoluminally deliverable medical device (not shown). Examples of endoluminally deliverable medical devices include stents, grafts, replacement heart valves, and the like, or any combination thereof.

The delivery system can include one or more tubular members for releasably constraining the medical device for endoluminal delivery and deployment. The delivery system 100 can, for example, include an elongated first tubular member 200 having a generally cylindrically shaped side wall defining a longitudinally extending lumen (not shown). The first tubular member 200 can have a delivery configuration, in which the medical device is placed within the lumen and constrained by the side wall toward a constrained state suitable for endoluminal delivery of the medical device. The delivery system 100 can also include an elongated second tubular member 300 having a generally cylindrically shaped side wall defining a longitudinally extending lumen (not shown). In the delivery configuration, the second tubular member 300 can be disposed between the first tubular member 200 and the medical device to limit expansion of medical device following removal or displacement of the first tubular member 200 from the delivery configuration. More specifically, the second tubular member 300 can limit expansion of the medical device toward an intermediate state that is larger than the constrained state and yet still smaller than a fully-deployed state, so as to allow axial and rotational positioning of the medical device at the treatment site prior to committing to a full deployment of the medical device. Examples of tubular members include catheters, sheaths, and introducers, or any elongate, tubular member used for supporting and endoluminally delivering a medical device. The tubular members can be constructed using any suitable material or combination of materials, such as polymers, polymer films, and braided wire structures, and any suitable methods known to those having ordinary skill in the art, such as injection molding, extrusion, flow-formed layered wraps, or any combination thereof.

Figure 1:
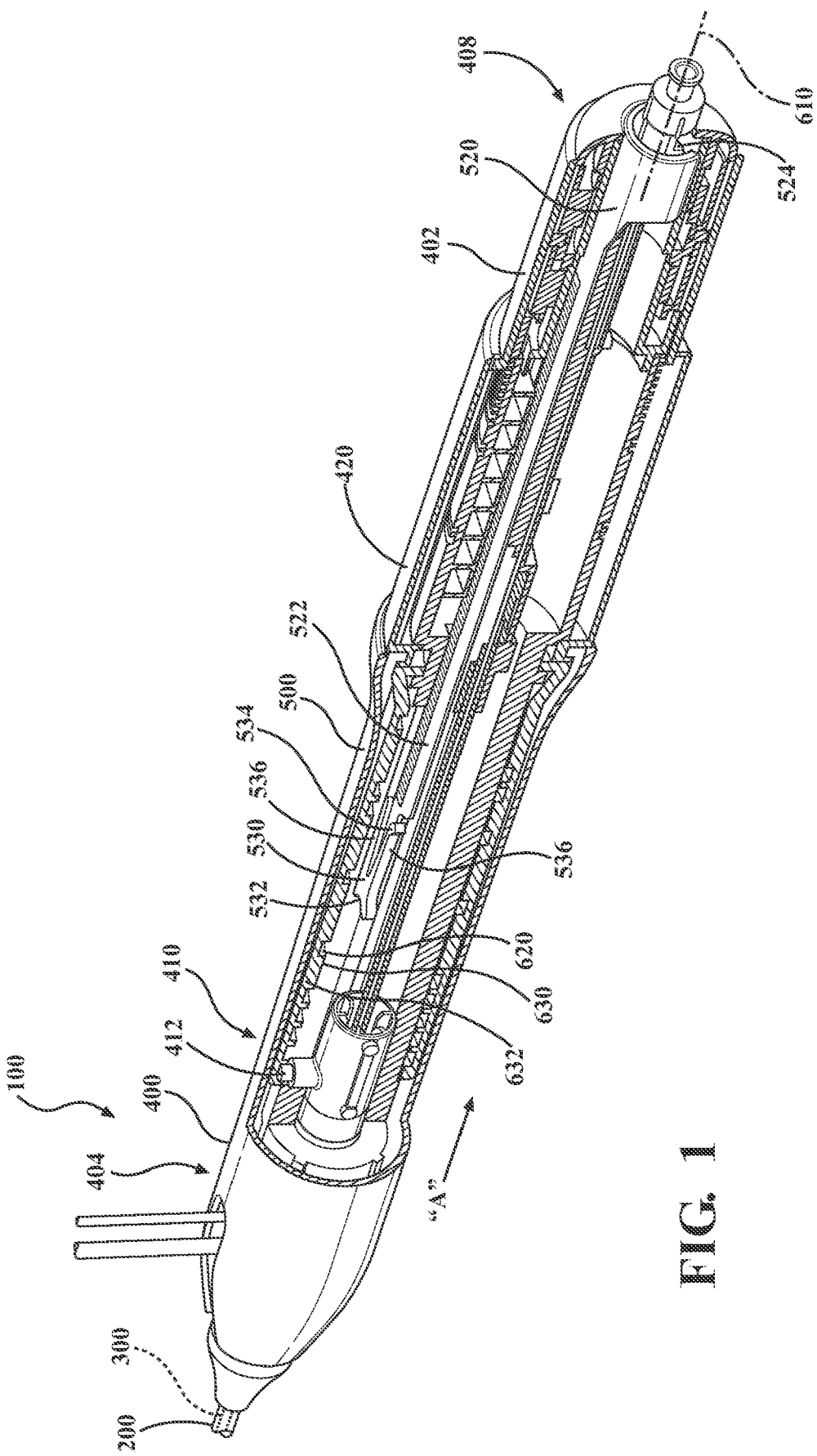
Figure 2:
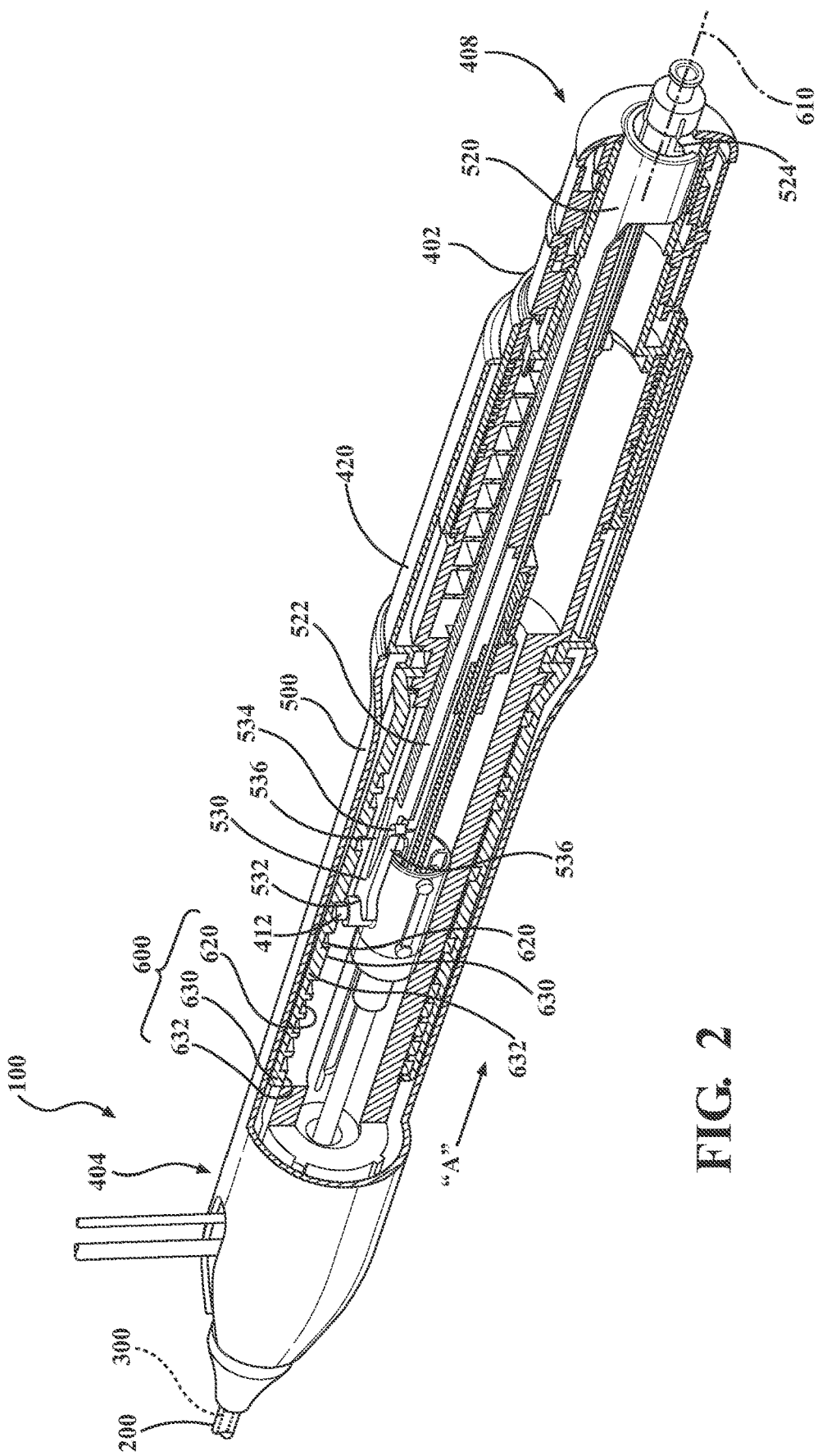
Figure 2A:
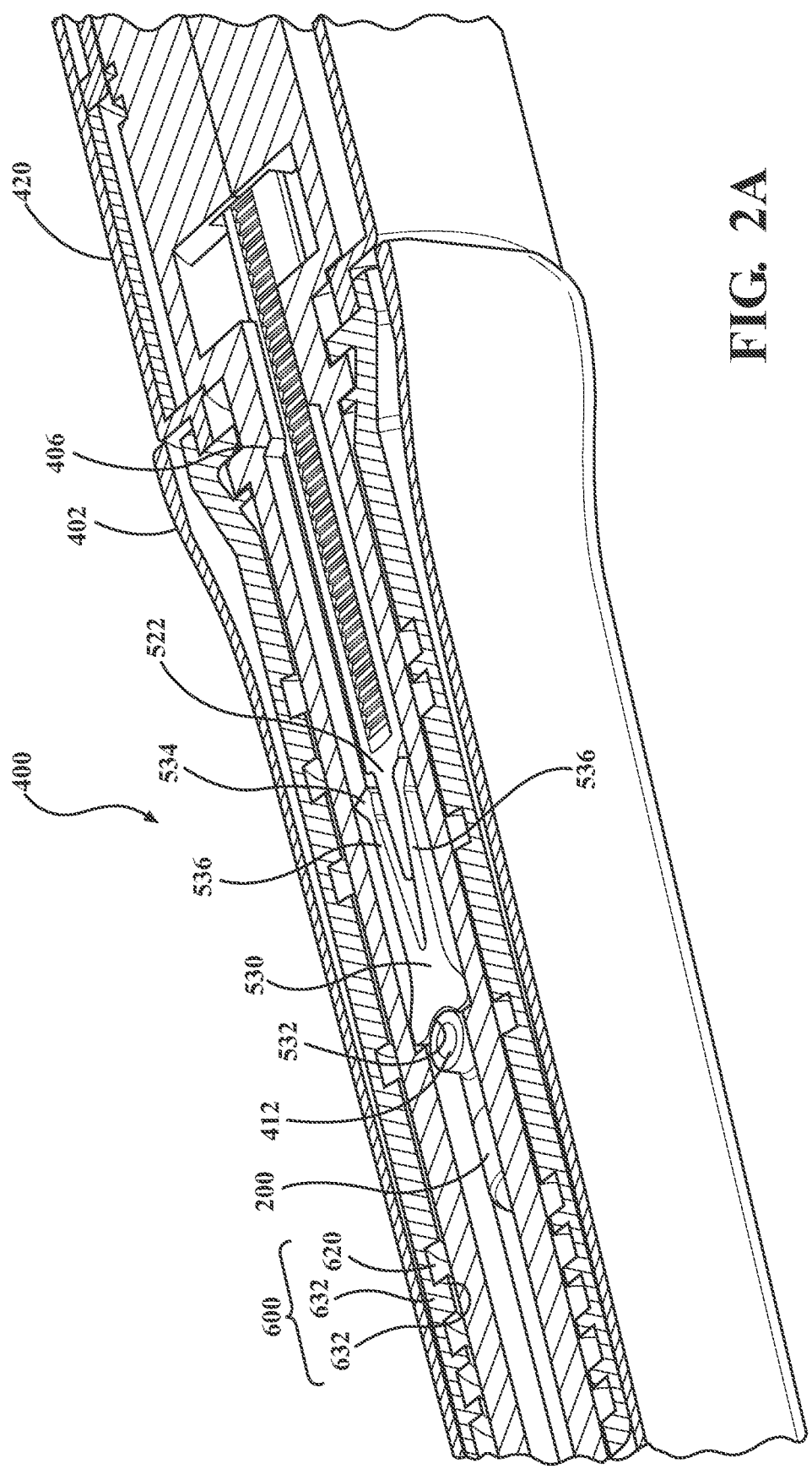
FIGS. 2A and 3A are enlarged views of FIGS. 2 and 3, respectively.
Figure 3:
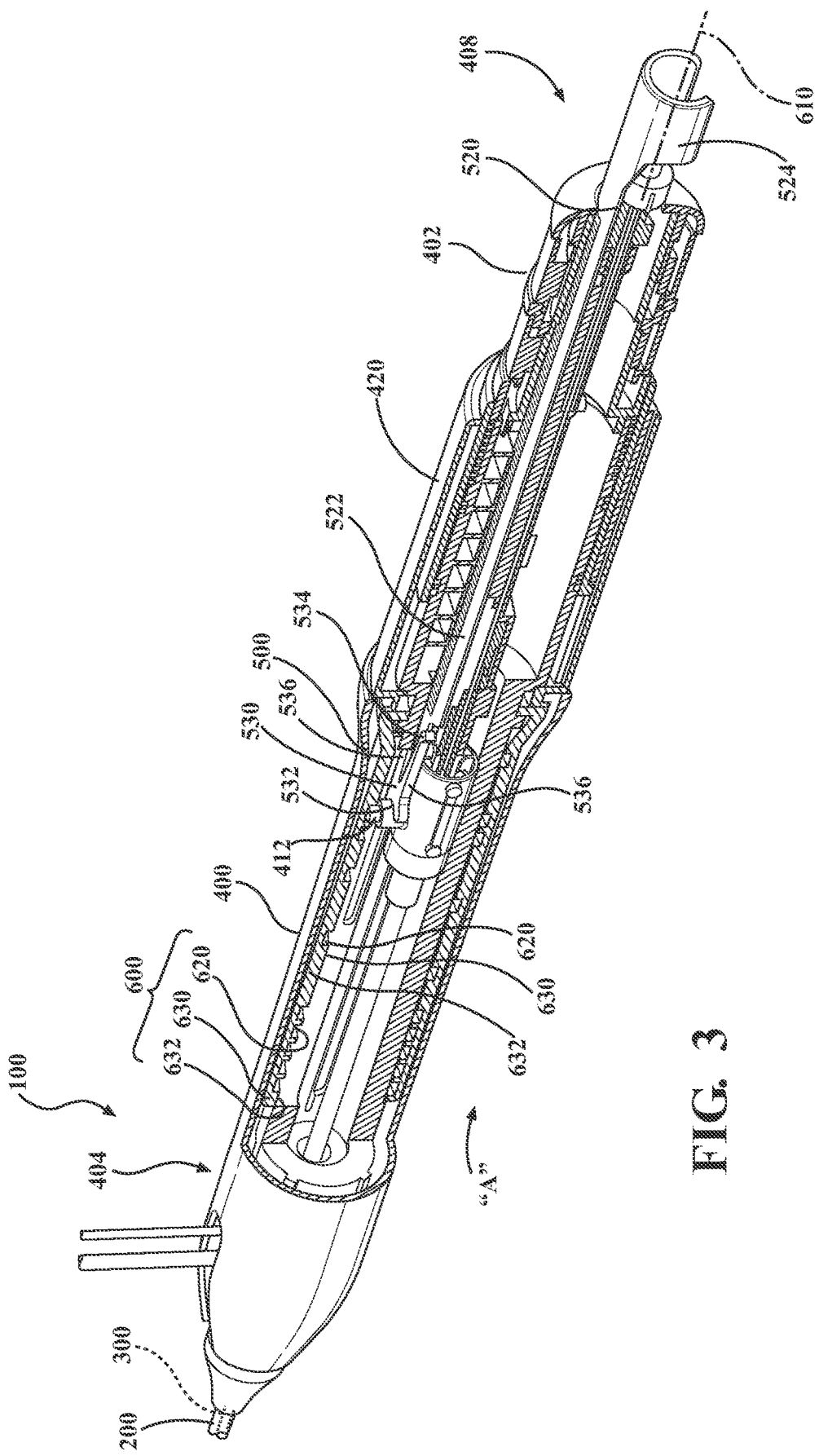
Figure 4:
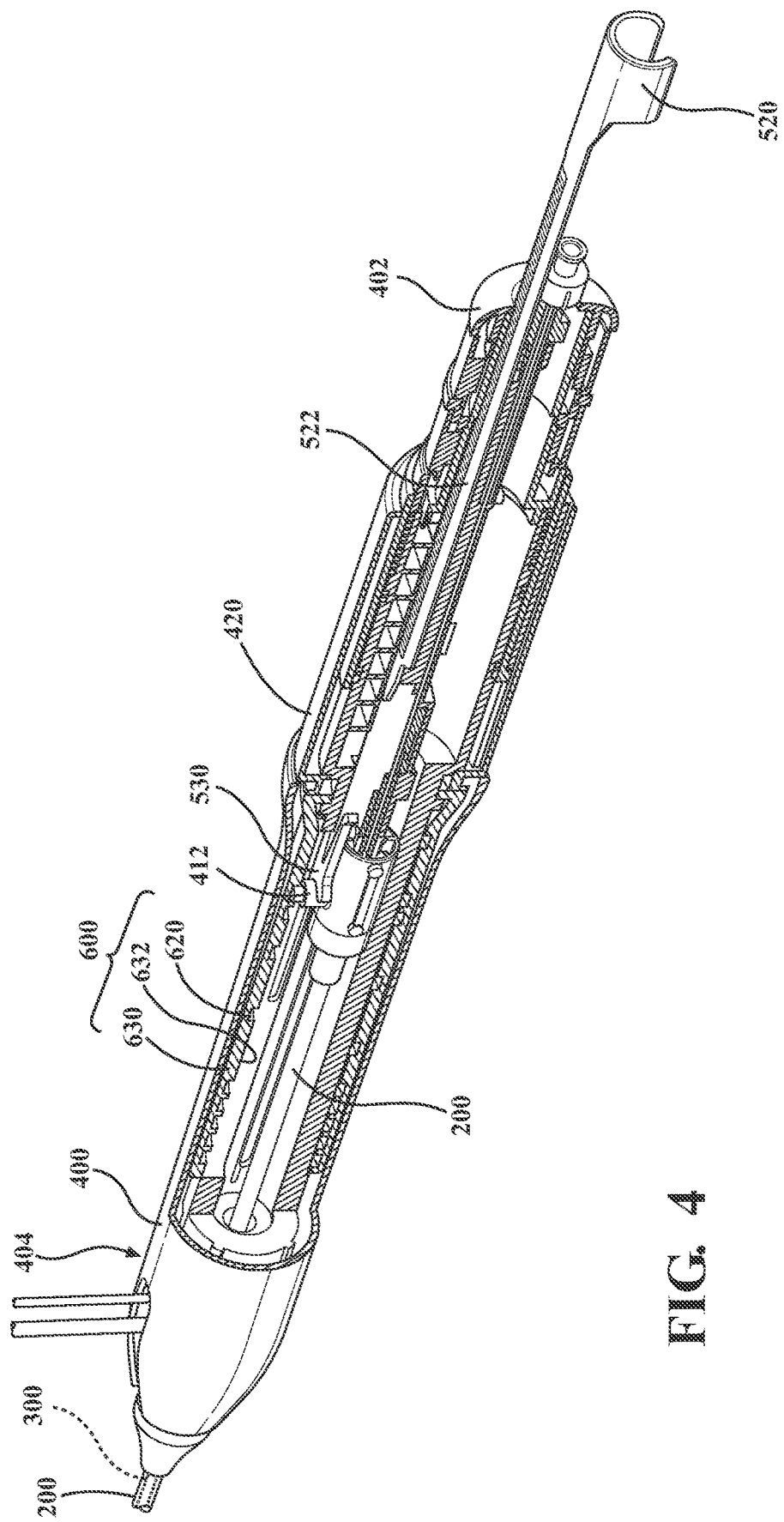

The delivery system includes a handle having actuators and interfaces, such as knobs, operable to facilitate displacement, removal or actuation of the first and second tubular members from their respective delivery configurations. Such a handle is disclosed in FIGS. 1-5 and generally indicated at 400. The handle 400 includes an outer housing 402. The handle 400 is disposed along and coupled to the proximal end of the catheter. The handle 400 includes a first actuator mechanism 410 and a first knob 420 for manual operation of the first actuator mechanism 410. The first actuator mechanism 410 includes a follower 412 that is axially displaceable as indicated by the arrow "A" in FIG. 1 in response to corresponding operation of the first knob 420. The follower 412 is, in turn, coupled to the first tubular member 200 to cause axial displacement of the first tubular member with the follower 412 during operation of the first knob 420. The first tubular member 200 is shown in FIG. 1 in the delivery configuration. In this configuration, the follower 412 is positioned at a distal portion 404 of the handle 400. Operation of the first knob 420 causes displacement of the first tubular member 200 with the follower 412 from the delivery configuration, as shown in FIG. 1, toward the proximal portion 408 of the handle 400, as shown in FIGS. 2-4.

Still referring to FIGS. 1-4, the handle 400 includes a second actuator mechanism 500 and a second knob 520 for manual operation of the second actuator mechanism 500. As shown in FIG. 1, with the first tubular member 200 in the delivery configuration, the second knob 520 is positioned and hidden at a proximal portion 408 of the handle 400. An arm 522 extends from the second knob 520 toward the distal portion 404 of the handle 400 for engaging the follower 412 during operation of the first actuator mechanism 410. As shown, in the delivery configuration, an end of the arm 522 can be spaced apart from the follower 412 to allow an initial displacement of the first tubular member 200 without causing corresponding displacement of the second knob 520 from the housing 402. The second knob 520 and arm 522 are supported by and slidably coupled to the housing 402 to allow displacement of the second knob 520 from the handle housing 402 during movement of the follower 412 with the first tubular member 200 between the positions shown in FIG. 1 and FIG. 3.

Optionally, a receiver 530 can be provided to support and locate the end of the arm 522 relative to the handle 400. A distal end 532 of the receiver 530 is configured to engage the follower 412 instead of the end of the arm 522, as previously discussed. The opposite proximal end 534 of the receiver 530 is defined by a pair of legs 536. The legs 536 are spaced apart to receive the end of the arm 522 therebetween.

The actuator mechanisms of the handle can include a variety of mechanisms for moving or actuating the tubular members in response to actuation of respective knobs of the handle. The first actuator mechanism 410 of the handle 400 shown in the figures, for example, includes a helically threaded positioner mechanism 600 for displacing the first tubular member 200 along an axis 610 in response to rotation of the first knob 420 about the axis 610.

The positioner mechanism 600 includes a helical slot or guide 620 formed along an inner surface 632 of a tubular wall 630 that extends from the first knob 420. The wall 630 and, therefore, the helical guide 620 rotate with the first knob 420. The follower 412 is disposed within a lumen defined by the wall 630, is engaged with the helical guide 620 and is rotatably constrained with respect to the axis 610, so that rotation of the helical guide 620 with the first knob 420 causes axial displacement of the follower 412 and the first tubular member 200 therewith, relative to the catheter and the second tubular member 300. Thus, rotation of the first knob 420 causes or allows progressive expansion of the medical device from the constrained state as the first tubular member 200 is retracted relative to the catheter from the delivery configuration of FIG. 1 to the various stages of displacement shown in FIGS. 2-3.

Figure 3A:
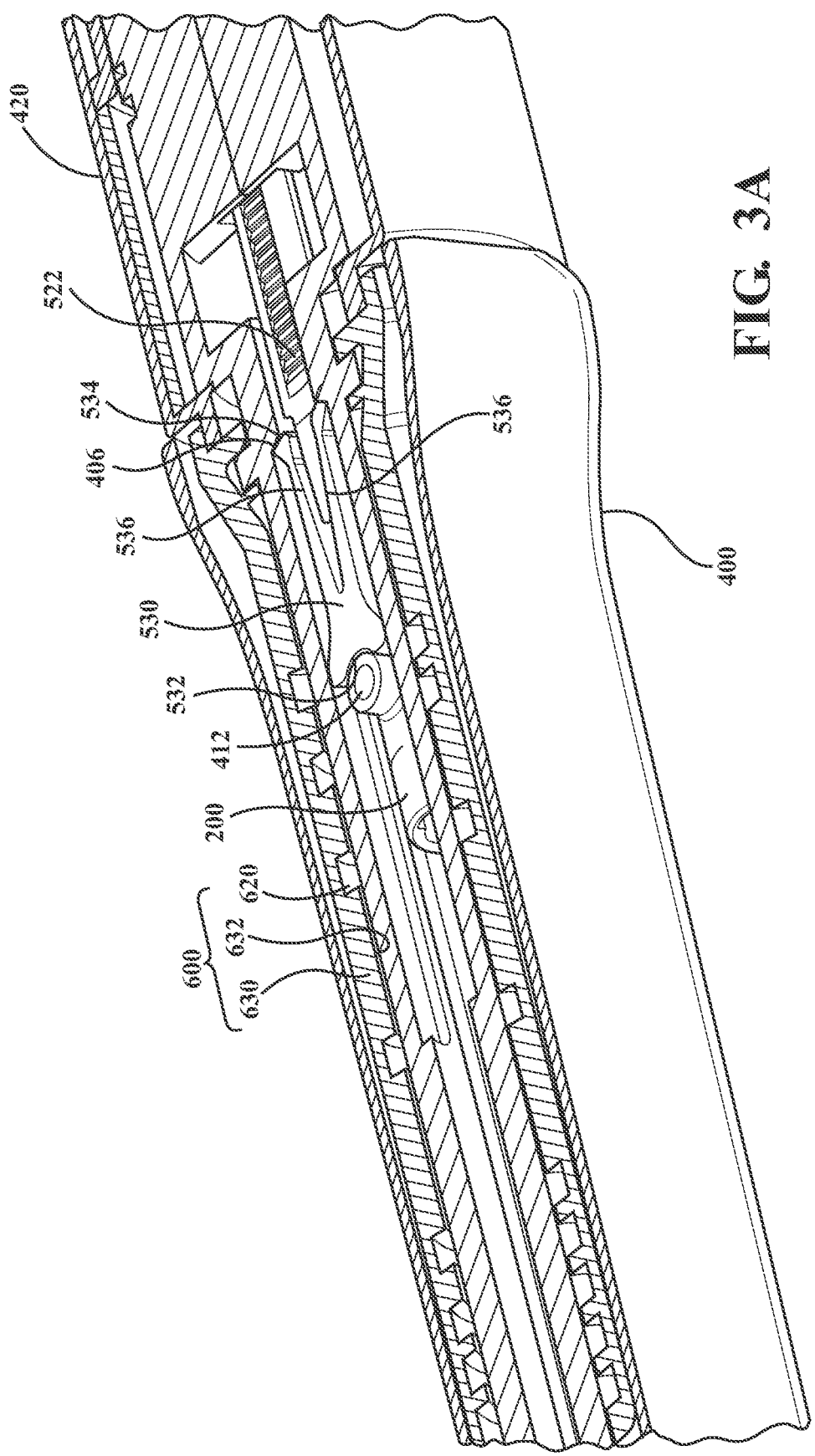

Referring to FIG. 3A, eventual engagement between the proximal end 534 of the receiver 530 and a locating surface 406 in the handle 400 provides a positive stop to prevent further axial displacement of the follower 412, first tubular member 200 and, in turn, further rotation of the first knob 420.

As earlier discussed, expansion of the medical device from the constrained state following removal of the first tubular member 200 is limited to the intermediate state by the second tubular member 300. Maintaining the medical device at the intermediate state allows axial or rotational positioning of the medical device at the treatment site prior to committing to full deployment.

The second tubular member 300 can also be axially retracted like the first tubular member. Alternatively, the second tubular member 300 can be formed from a film sleeve held together by an elongated member (not shown), such as a deployment wire or fiber. An example of the latter arrangement is disclosed in U.S. Pat. No. 6,352,561 to Leopold et al., the content of which is incorporated herein by reference in its entirety. In either case, the second actuating mechanism 500 may be provided as a coupling between the second knob 520 and the second tubular member 300 and/or the elongated member, so that removing the second knob 520 from the handle 400 causes removal and/or opening or otherwise actuation of the second tubular member 300.

In operation, the first knob 420 is rotated to actuate the threaded positioner mechanism 600 and cause displacement of the first tubular member 200 from the position in FIG. 1 toward the position in FIG. 3. As earlier discussed, the follower 412 is initially spaced apart from the end of the arm 522. Thus, the second knob 520 remains undisturbed and hidden inside the outer housing 402 near the proximal portion 408 of the handle 400 during initial actuation of the first knob 420 to prevent use of the second knob 520.

Displacement of the first tubular member 200 relative to the medical device allows the medical device to expand from the constrained state toward the second tubular member 300, which limits expansion of the medical device to the intermediate state. In this state, the clinician may choose to make final axial and/or rotational adjustments of the position of the medical device prior to full deployment of the medical device. Once the medical device is placed at a desired position at the treatment site, the clinician can continue to operate the first knob 420.

Eventually, as shown in FIG. 2, the follower 412 contacts the end of the arm 522 so that continued operation of the first knob 420 and movement of the first tubular member 200 translates into displacement of the second knob 520 from the outer housing 402, as shown in FIG. 3, wherein the second knob 520 is presented for use by the clinician. The second knob 520 and arm 522 can be removed and separated from the handle 400, as shown in FIGS. 4 and 5, to cause displacement and/or otherwise opening of the second tubular member 300 to allow expansion of the medical device toward engagement with surrounding vessel tissue.

The second knob 520 can include a slot 524 to accommodate use of a guidewire (not shown), which allows the second knob 520 to be substantially coaxial or otherwise near the axis 610.

After full deployment of the medical device, the handle 400 can be separated from the first tubular member 200 to allow the first tubular member 200 to be used as an introducer sheath for other medical devices or related surgical implements.

It will be apparent to those skilled in the art that various modifications and variations can be made in the present disclosure without departing from the spirit or scope of the present disclosure. Thus, it is intended that the present disclosure cover the modifications and variations of this present disclosure provided they come within the scope of the appended claims and their equivalents.

What is claimed is:

1. A delivery system for endoluminal delivery of an expandable device, the delivery system comprising:
  a catheter having a proximal end and an opposite distal end, the distal end configured to support the expandable device;
  a primary sheath having a delivery position in which the primary sheath constrains the expandable device toward a collapsed configuration suitable for endoluminal delivery;
  a handle including a first actuator that is actuatable to cause the expandable device to expand from the collapsed configuration, the handle further including a second actuator for operating one or more functions of the handle, wherein the second actuator is initially hidden to prevent actuation of the second actuator prior to the expandable device expanding and is configured to be revealed when the expandable device is expanded, the second actuator being actuatable once revealed; and
  a follower and a positioner actuator, the positioner actuator having a tubular wall having a longitudinal axis and an inner surface defining a lumen extending along the longitudinal axis, the lumen being configured to receive the primary sheath and the follower therethrough.

2. The delivery system of claim 1, the handle further including a housing, wherein the second actuator is initially hidden within the housing to prevent actuation of the second actuator prior to the expandable device expanding, the second actuator being displaceable relative to the housing as a result of causing the expandable device to expand, wherein the second actuator is revealed and actuatable as a result of being displaced relative to the housing.

3. The delivery system of claim 1, wherein the first actuator is actuatable to cause an axial displacement of the primary sheath along the catheter from the delivery position, wherein the second actuator is initially hidden to prevent actuation of the second actuator prior to the primary sheath being displaced along the catheter from the delivery position, and wherein the second actuator is revealed as a result of the primary sheath being displaced along the catheter from the delivery position.

4. The delivery system of claim 1, further including a secondary sheath having a delivery position in which the secondary sheath limits expansion of the expandable device to an intermediate configuration larger than the collapsed configuration and smaller than a fully deployed configuration, and wherein the one or more functions of the handle includes deployment of the secondary sheath to allow deployment of the expandable device from the intermediate configuration.

5. The delivery system of claim 4, wherein the second actuator is removable from the handle, and wherein removal of the second actuator causes a removal of the secondary sheath and a deployment of the expandable device toward the fully deployed configuration.

6. The delivery system of claim 1, further including an arm for engaging the primary sheath, the arm extending from the second actuator and being operable to engage with the follower coupled to the primary sheath such that the arm causes the second actuator to be revealed as a result of causing the primary sheath to be axially displaced from the delivery position.

7. The delivery system of claim 6, wherein the follower and the arm are spaced apart when the primary sheath is in the delivery position, so that the second actuator is revealed after an initial delay following at least a partial deployment of the expandable device.

8. The delivery system of claim 7, wherein the second actuator is a knob.

9. The delivery system of claim 1, wherein the inner surface includes a helically extending slot for engaging the follower, wherein rotation of the tubular wall about the longitudinal axis causes axial displacement of the primary sheath and the follower along the longitudinal axis.

10. A delivery system for endoluminal delivery of an expandable device, the delivery system comprising:
 a catheter configured to support the expandable device constrained toward a collapsed configuration suitable for endoluminal delivery;
 a primary sheath operable to constrain the expandable device toward the collapsed configuration; and
 a handle including a first actuator that is actuatable to cause the expandable device to expand from the collapsed configuration, the handle further including a second actuator for operating one or more functions of the handle,
 wherein the second actuator is operable to be positioned in a hidden configuration and a revealed configuration,
 wherein operation of the first actuator displaces the second actuator from the hidden configuration to the revealed configuration, and
 wherein the primary sheath is operable to displace the second actuator from the hidden configuration to the revealed configuration when the first actuator is actuated.

11. The delivery system of claim 10, wherein the first actuator is operable to displace the primary sheath.

12. The delivery system of claim 10, wherein the handle is separatable from the primary sheath such that the primary sheath may be implemented as an introducer sheath.

13. The delivery system of claim 12, further including an arm for engaging the primary sheath, the arm extending from the second actuator and being operable to engage with a follower coupled to the primary sheath such that the arm causes the second actuator to be revealed as a result of causing the primary sheath to be axially displaced from the delivery position.

14. The delivery system of claim 12, further comprising a follower and a positioner actuator, the positioner actuator having a tubular wall having a longitudinal axis and an inner surface defining a lumen extending along the longitudinal axis, the lumen being configured to receive the primary sheath and the follower therethrough.

15. The delivery system of claim 10, wherein the second actuator includes a slot operably to accommodate a guidewire.

16. The delivery system of claim 10, wherein the second actuator is substantially coaxial with the handle.

17. A delivery system for endoluminal delivery of an expandable device, the delivery system comprising:
 a catheter having a proximal end and an opposite distal end, the distal end configured to support the expandable device;
 a primary sheath having a delivery position in which the primary sheath constrains the expandable device toward a collapsed configuration suitable for endoluminal delivery;
 a handle including a first actuator that is actuatable to cause the expandable device to expand from the collapsed configuration, the handle further including a second actuator for operating one or more functions of the handle, wherein the second actuator is initially hidden to prevent actuation of the second actuator prior to the expandable device expanding and is configured to be revealed when the expandable device is expanded, the second actuator being actuatable once revealed;
 a follower coupled to the primary sheath such that actuation of the first actuator reveals the second actuator via the follower moving away from the distal end of the catheter and mechanically engaging the second actuator to reveal the second actuator.

* * * * *